US008983588B2

(12) United States Patent
Addison et al.

(10) Patent No.: US 8,983,588 B2
(45) Date of Patent: Mar. 17, 2015

(54) SIGNAL ANALYSIS

(75) Inventors: Paul Stanley Addison, Lothian (GB); James Nicholas Watson, Fife (GB)

(73) Assignee: Cardiodigital Limited, East Lothian (GB)

(*) Notice: Subject to any disclaimer, the term of this patent is extended or adjusted under 35 U.S.C. 154(b) by 1956 days.

(21) Appl. No.: 11/815,933

(22) PCT Filed: Feb. 10, 2006

(86) PCT No.: PCT/GB2006/050033
§ 371 (c)(1),
(2), (4) Date: Sep. 24, 2008

(87) PCT Pub. No.: WO2006/085120
PCT Pub. Date: Aug. 17, 2006

(65) Prior Publication Data
US 2009/0204162 A1 Aug. 13, 2009

(30) Foreign Application Priority Data
Feb. 10, 2005 (GB) ................................. 0502871.7

(51) Int. Cl.
*A61B 5/0402* (2006.01)
*A61B 5/0452* (2006.01)
*A61N 1/39* (2006.01)
*A61B 5/00* (2006.01)
*A61B 5/046* (2006.01)
*A61B 5/0464* (2006.01)

(52) U.S. Cl.
CPC ............... *A61B 5/0452* (2013.01); *A61B 5/726* (2013.01); *A61N 1/3925* (2013.01); *A61B 5/046* (2013.01); *A61B 5/0464* (2013.01)
USPC .................... 600/510; 600/509; 607/4; 607/5

(58) Field of Classification Search
USPC .................................. 607/4, 5; 600/509, 510
See application file for complete search history.

(56) References Cited

U.S. PATENT DOCUMENTS

| 6,171,257 | B1 * | 1/2001 | Weil et al. ...................... 600/518 |
| 6,438,419 | B1 * | 8/2002 | Callaway et al. .................. 607/5 |
| 6,961,612 | B2 * | 11/2005 | Elghazzawi et al. .............. 607/6 |
| 2004/0215244 | A1 | 10/2004 | Marcovecchio et al. |

FOREIGN PATENT DOCUMENTS

| WO | WO01/82099 A1 | 11/2001 |
| WO | WO2005/096170 A1 | 10/2005 |

OTHER PUBLICATIONS

Addison, P.S. et al., Evaluating Arrhythmias in ECG Signals Using Wavelet Transforms Real-Time Analysis of the Ventricular Fibrillation Waveform Can Reveal Hidden Structures, IEEE Engineering in Medicine and Biology Magazine, Sep. 2000, pp. 104-109, vol. 19, No. 5, IEEE Service Center, Pisacataway.

(Continued)

Primary Examiner — Tammie K Heller
(74) Attorney, Agent, or Firm — W. Kevin Ransom; Moore & Van Allen PLLC

(57) ABSTRACT

A method of analysis of medical signals is presented which provides useful clinical information concerning the state of the myocardium during cardiopulmonary resuscitation (CPR). The analysis during CPR can be used to (i) identify the underlying rhythm, (ii) provide a measure of the efficacy of CPR, and (iii) to predict the outcome from a defibrillation shock.

39 Claims, 8 Drawing Sheets

(56) References Cited

OTHER PUBLICATIONS

International Search Report, PCT/GB2006/050033, Jun. 23, 2006.

Berg, R. A., Hilwig, R. W., Kern, K. B. et al., "Precountershock cardiopulmonary resuscitation improves ventricular fibrillation median frequency and myocardial readiness for successful defibrillation from prolonged ventricular fibrillation: A randomised, controlled swine study." Ann Emerg Med 2002; 40: 563-571.

Achleitner, U., Wenzel, V., Strohmenger, H. U. et al., "The Beneficial effect of basic life support on ventricular fibrillation mean frequency and coronary perfusion pressure." Resuscitation 2001; 51: 151-158.

Kolarova, J., Ayoub, I. M., Yi, Z. et al., "Optimal timing for electrical defibrillation after prolonged untreated ventricular fibrillation." Crit Care Med. 2003; 31: 2022-2028.

Eftestol, T., Wik, L., Sunde, K., Steen, P. A., "Effects of CPR on predictors of VF defibrillation success during out-of-hospital cardiac arrest." Circulation 2004; 110: 10-15.

Sunde, K., Eftestol, T., Askenberg, C., Steen, P.A., "Quality assessment of defibrillation and advanced life support using data from the medical control module of the defibrillator." Resuscitation 1999; 41: 237-247.

Wik, L., Hansen, T. B., Fylling, F., Steen, T., Vaagenes, P., Auestad, B. H., Steen, P. A., "Delaying defibrillation to give basic cardiopulmonary resuscitation to patients with out-of-hospital ventricular fibrillation—A randomized trial." JAMA 2003; 289 (11): 1389-1395.

Cobb, L. A., Fahrenbruch, C. E., Walsh, T. R. et al., "Influence of cardiopulmonary resuscitation prior to defibrillation in patients with out-of-hospital ventricular fibrillation." JAMA 1999; 281 (13): 1182-1188.

Eftestol, T., Sunde, K., Steen, P. A., "Effects of interrupting precordial compressions on the calculated probability of defibrillation success during out-of-hospital cardiac arrest." Circulation 2002; 105: 2270-2273.

Aase, S. O., Eftestol, T., Husoy, J. H., Sunde, K., Steen, P. A., CPR artifact removal from human ECG using optimal multichannel filtering. IEEE Trans Biomed Eng. Nov. 2000; 47 (11): 1440-9.

Eilevstjonn, J., Eftestol, T., Aase, S. O., Myklebust, H., Husoy, J. H., Steen, P.A., Feasibility of shock advice analysis during CPR through removal of CPR artefacts from the human ECG. Resuscitation May 2004; 61 (2): 131-41.

Addison, P. S., "The Illustrated Wavelet Transform Handbook: Introductory Theory and Applications in Science, Engineering, Medicine and Finance." Institute of Physics Publishing 2000; Bristol, UK.

Frenneaux, M., "Cardiopulmonary resuscitation—some physiological considerations"; Resuscitation (58); 2003: 259-265.

Watson, J. N., Addison, P. S., Clegg, G. R., Holzer, M., Sterz, F., and Robertson, C. E., "A novel wavelet transform based analysis reveals hidden structure in ventricular fibrillation." Resuscitation 2000; 43:121-127.

Addison, P. S., Watson, J. N., Clegg, G. R., Steen, P. A., Robertson, C. E., Finding coordinated atrial activity during ventricular fibrillation using wavelet decomposition. IEEE Engineering in Medicine and Biology 2002; 21: 58-65.

* cited by examiner (a)

(b)

(c)

SIGNAL ANALYSIS

BACKGROUND OF THE INVENTION

1. Field of the Invention

The present invention relates to improvements in or relating to signal analysis, in particular to a method for the analysis of the electrocardiogram (ECG) during cardiopulmonary resuscitation (CPR).

2. Description of the Related Art

Despite improvements in the rapidity with which shocks are delivered and the shock characteristics themselves, results achieved from the treatment of cardiac arrest remain suboptimal. For the past two decades, therefore, efforts have been made to characterise the ECG waveform during cardiac arrest in an attempt to optimise shock delivery and outcome.

Experimental [1,2,3] and clinical [4] studies have indicated that administering Cardiopulmonary Resuscitation (CPR) prior to shock therapy can increase the likelihood of successful defibrillation for established ventricular fibrillation (VF). Further studies have suggested that delaying CPR for a defibrillation attempt may cause a dramatic decrease in the likelihood of defibrillation success [5]. These results are consistent with clinical studies [6,7] which indicate that pre-shock CPR can improve the rates of return of spontaneous circulation (ROSC) and survival to hospital discharge when emergency medical services (EMS) response times exceeded 4-5 minutes.

There is therefore a shift in emphasis in resuscitation protocols with uninterrupted CPR taking a more prevalent roll. Specifically, there is recognition that, while defibrillation is the only effective means of reverting the heart to normal sinus rhythm, maximising the quantity and quality of CPR and reducing the 'hands-free' periods where CPR is not delivered has a substantial bearing on the likely efficacy of defibrillation therapy.

In current resuscitation protocols CPR is regularly halted for a period of time (up to 20 or 30 seconds) in order to identify whether the patient should receive a defibrillation shock, i.e. whether the underlying myocardial rhythm is of a type that is shockable such as VF or ventricular tachycardia (VT) or non-shockable such as Asystole or pulseless electrical activity (PEA). It has been shown recently that this cessation of CPR, during which the ECG trace is analysed, can inhibit the effectiveness of any subsequent defibrillation attempt [8].

Accordingly there is a need for a technique which can effectively analyse the underlying cardiac signal during CPR. Adaptive filters have been used by others in an attempt to filter the ECG of CPR artefact using available secondary signals (e.g. accelerometer). However, these methods typically involve digital filters with coefficients that have evolved from averaged historic data (Wiener-like) [9] or linearly scaled super-positioning of reference data, and often tap-delayed reference data when the system is assumed to be non-causal, for best signal approximation (Matching pursuit-like) [10].

The former (Wiener-like) is highly likely to have considerable residuals due to the non-stationary nature of the artefact signal. This will necessarily leave artefact in the de-noised trace making rhythm identification difficult. This is particularly the case for asystole. The latter (Matching pursuit-like) will have either residual artefact components if too few iterations of the MP algorithm are executed or it will lose components of the underlying myocardium rhythm if too many approximation iterations are applied. Often the practical identification of this 'depth of recursion' parameter is not fully discussed in published literature.

BRIEF SUMMARY OF THE INVENTION

According to a first aspect of the present invention, there is provided a method of signal analysis comprising the steps of:
deriving an electrocardiogram (ECG) signal from a subject during Cardio-Pulmonary Resuscitation (CPR);
deriving a time-scale transform surface of the ECG; and
analysing a characteristic measure of the transform surface to identify the type of underlying myocardial rhythm.

According to a second aspect of the present invention, there is provided an apparatus for signal analysis comprising: sensor means suitable to derive an electrocardiogram (ECG) signal from a subject; signal processing means suitable for deriving a wavelet scalogram from the ECG; and computational analysis means suitable for deriving a time-scale transform surface of the ECG and analysing a characteristic measure of the transform surface to identify the type of underlying myocardial rhythm.

The apparatus of the second aspect comprises further means as detailed below.

In a third aspect, the apparatus of the second aspect can form part of or be incorporated for use with a defibrillator.

Furthermore, in a fourth aspect there is provided a computer program product encoded with instructions that when run on a computer puts into effect signal processing means suitable for deriving a wavelet scalogram from the ECG; and computational analysis means suitable for deriving a time-scale transform surface of the ECG and analysing a characteristic measure of the transform surface to identify the type of underlying myocardial rhythm.

The computer program product comprises further means as detailed below.

Preferably, the step of analysing a characteristic measure of the transform surface comprises the use of empirically derived heuristics.

Preferably, said characteristic measure is obtained by the manipulation of the coefficients obtained from the ECG time-scale surface calculated over one or more of the surface scales.

Preferably, said characteristic measure is derived from a set of coefficients of a modulus maxima representation which are re-ordered in order of their magnitude.

Preferably, the method further comprises comprising plotting said re-ordered coefficients as a curve, and wherein said characteristic measure is the slope across a selected portion of the curve.

Preferably, the method comprises plotting said re-ordered coefficients as a curve, and wherein said characteristic measure is the value of a single coefficient at a specified point in the curve.

Preferably, the method comprises plotting said re-ordered coefficients as a curve, and wherein said characteristic measure is a median, mode or mean of several values taken from a specified region on the curve.

Preferably, analysis is undertaken of the characteristic measure to determine whether the underlying myocardial rhythm is shockable or non-shockable.

Preferably, said analysis is characterised by the comparison of the characteristic measure against a threshold value.

Preferably, said type of underlying myocardial rhythm is one of ventricular fibrillation, ventricular tachycardia, asystole, pulseless electrical activity or a sinus rhythm.

Preferably, said analysis is characterised by the comparison of the derived characteristic measure against those typical of known rhythm type.

Preferably, said typical values describe the shape of typical curves associated with underlying myocardial rhythm types.

Preferably, the method further comprises the steps of:
deriving a reference signal from a subject during CPR;
deriving a time-scale transform surface of the reference signal; and
using the time-scale transform surface of the reference signal to filter the time-scale transform surface of the ECG before analysing said characteristic measure.

Preferably, said reference signal represents an electrical measurement.

Preferably, said electrical measurement is the subject's trans-thoracic impedance.

Preferably, said reference signal represents a mechanical measurement.

Preferably, said mechanical measurement is a force measurement of the chest during CPR.

Preferably, said force measurement is obtained from strain gauge sensors.

Preferably, said mechanical measurement is derived from an acceleration measurement of the patient during CPR.

Preferably, the step of filtering the time-scale transform surface of the ECG comprises the cancelling or negating of coefficient values within the ECG surface when coefficient values in the reference signal's transform surface that are proximal in time and scale to the coefficient values within the ECG surface fulfil a predetermined criterion.

Preferably, said criterion is the coefficient amplitude being above a given threshold.

Preferably, the step of filtering the time-scale transform surface of the ECG comprises the scaling of coefficient values within the ECG surface with respect to the coefficient values in the reference signal's transform surface which are proximal in time and scale.

Preferably, the step of filtering the time-scale transform surface of the ECG comprises a suppression of redundant or superfluous coefficient values within the ECG surface.

Preferably, said suppression of coefficient values utilises modulus maxima techniques.

Preferably, said time-scale transform is the wavelet transform.

Preferably, said wavelet transform is a continuous wavelet transform.

Preferably, said characteristic measure includes the median coefficient value of a number of the highest coefficient values from one or more of the ECG time-scale scales Preferably, said characteristic measure is computed from coefficients associated with scales with characteristic frequencies above that of the typical fibrillating frequency of the heart.

Preferably, said characteristic measure is computed from coefficients associated with scales of characteristic frequencies above that of the typical frequency of CPR.

Preferably, said characteristic measure includes an entropy measure.

Preferably, said entropy measure is of the form:

$$WE_a = \frac{\int \ln|T(a,b)|_a \, db}{\int |T(a,b)|_a \, db}$$

(Where, $|T(a,b)|_a$ are the wavelet transform modulus values at scale a.)

Preferably, said entropy measure is computed from coefficients associated with scales with characteristic frequencies above that of the typical fibrillating frequency of the heart.

Preferably, the method comprises the step of analysing the measured characteristic to determine the ongoing efficacy of the CPR.

Preferably, the method comprises the step of analysing the measured characteristic to perform a defibrillation shock outcome prediction.

BRIEF DESCRIPTION OF THE DRAWINGS

The present invention will now be described, by way of example only, with reference to the accompanying drawings, which show the following:

FIG. 3: (b) The Modulus Maxima scalogram. (Horizontal axis=time in seconds. Vertical axis=Characteristic wavelet frequency in Hz.)

FIG. 4: (b) Schematic of the secondary reference signal modulus maxima surface (Horizontal axis=time in seconds. Vertical axis=wavelet scale.)

FIG. 4: (c) Schematic of the filtered ECG modulus maxima surface with CPR components removed (Horizontal axis=time in seconds. Vertical axis=wavelet scale.)

FIG. 7: (b) The Wavelet Transform of the signal in (a). (Horizontal axis=time in seconds. Vertical axis=Characteristic wavelet frequency in Hz.)

FIG. 7: (c) Wavelet characteristic measure values during the CPR episode. The shockable/non-shockable rhythm threshold is shown by the dashed line. Shockable rhythms are identified as those where the characteristic measure falls above the line. (Horizontal axis=time in seconds. Vertical axis=Marker value in arbitrary units.)

DETAILED DESCRIPTION OF THE INVENTION

Figure 1:
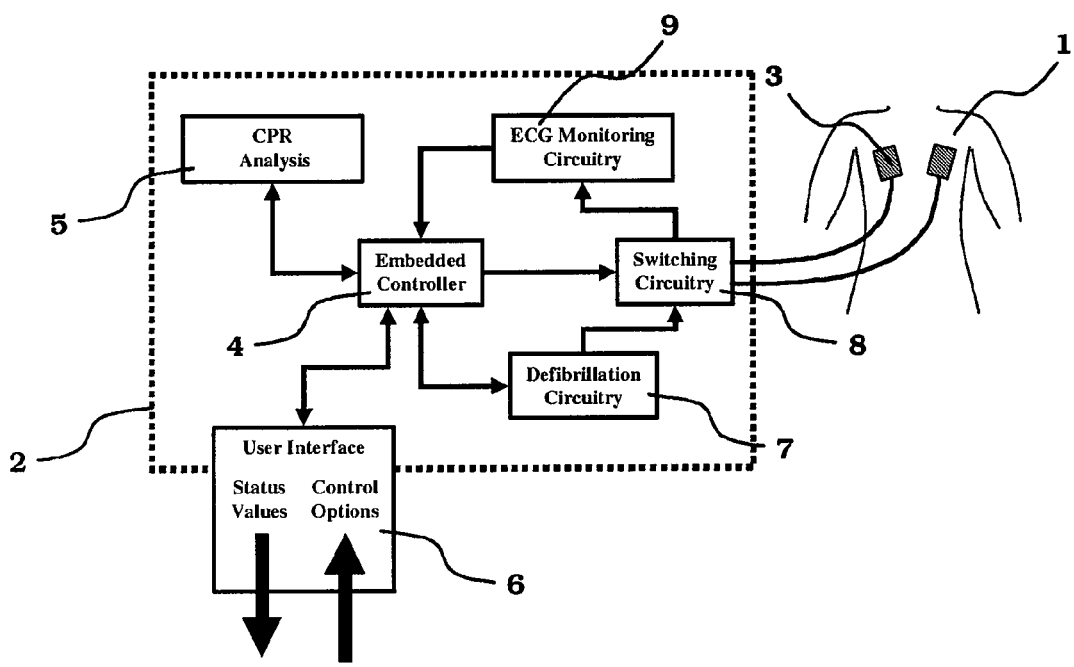
FIG. 1: Schematic block diagram of a defibrillator with reference to the current invention.

The present analysis method avoids the need to stop CPR to identify the underlying cardiac rhythm and provide metrics for determining the most appropriate patient treatment. In addition, such an analysis method will allow for the prediction of defibrillation shock therapy outcome during CPR. Such an analysis method will also provide information on the efficacy of the ongoing CPR by monitoring changes in the metric values through time.

In the present invention we employ a time-scale transform based method. A time-scale transform analysis of the ECG is especially valuable because of its ability to elucidate simultaneously local spectral and temporal information from a signal [11]. An improvement in the partitioning of signal components is observed using time-scale techniques due to this fundamental difference between a time-scale transform and alternative prior art methods discussed above. While these alternatives, in some form or another, characterize an aspect of the behaviour of the signal over a period of time, however short, the time-scale method can identify pertinent information highly localised in time. Hence, superior temporal partitioning of salient aspects of the transformed ECG becomes achievable prior to any classification step.

One particular type of preferred time-scale transform is the wavelet transform. The advantages that wavelet transform analysis can provide over the alternative methods include:

Optimal time-frequency decomposition: allowing scale (characteristic frequency) dependent filtering in time to be applied.

Intrinsic and optimal signal smoothing in time: such that temporal smoothing is dependent upon the scale under investigation.

Linear transform: the wavelet transform is a linear transform allowing direct comparisons of scalograms for filtering purposes.

Signal reconstruction: the continuous wavelet transform reconstruction formula is complete allowing signal reconstruction from the filtered scalogram where necessary.

Information from a time-scale transform representation, in particular a wavelet transform representation, allows for advanced time-frequency partitioning of the signal components.

In WO 2005/096170 Addison and Watson teach a method for employing a modulus maxima technique to analyse the ECG exhibiting VF and obtain a shock outcome prediction. The method uses an entropy measure to characterise the ECG waveform. This measure is subsequently used as an input to a classifier to predict the likelihood of a successful outcome from defibrillation shock therapy. However, this method is specific to regions of the ECG not containing CPR artefact. During periods of CPR, the CPR artefact produces many modulus maxima lines which typically dominate, in terms of their energy, those of the underlying cardiac rhythm and so markedly degrades the performance of the method of WO 2005/096170.

In WO 2001/82099 Addison and Watson teach a method of analysis of the VF waveform during CPR for the prediction of defibrillation shock outcome during episodes of ventricular fibrillation. By contrast the present method allows the identification of the underlying cardiac rhythm during CPR and a measure of the efficacy of CPR.

In a further departure from WO 2001/82099, one preferred embodiment of the current invention utilises a reference signal or reference signals associated with CPR. Such reference signals may include accelerometer or strain gauge information indicating the depth of CPR compression, trans-thoracic impedance measurements or common mode voltages. All such measures provide additional data reflecting the characteristics of the applied CPR. The reference signal selected is also transformed into the time-scale domain and used to suppress the CPR artefact components in the transform of the original ECG signal. In this way the CPR artefact can be filtered out leaving the salient information of the underlying rhythm more accessible to subsequent analysis. The suppression can be carried out by a number of means including interrogation of the modulus maxima components associated with the wavelet transform of both the ECG signal and the reference signal.

When no reference signal is available, CPR components are negated using empirically derived heuristics.

Specifically, the current invention uses wavelet transform-based methods to analyse the signal in order to:
identify the underlying rhythm during CPR
indicate the efficacy of the ongoing CPR
predict the outcome of subsequent defibrillation therapy during CPR In general, the present method provides an improved method for analysis of the ECG during CPR for clinically useful purposes. A preferred method employs the continuous wavelet transform to separate out the temporal signal components in to a time-frequency representation to aid subsequent analysis. The wavelet transform of a signal x(t) is defined as:

$$T(a,b) = \frac{1}{\sqrt{a}} \int_{-\infty}^{+\infty} x(t)\psi^*\left(\frac{t-b}{a}\right) dt \qquad [1]$$

where $\psi^*(t)$ is the complex conjugate of the wavelet function $\psi(t)$, a is the dilation parameter of the wavelet and b is the location parameter of the wavelet. The scalogram is the time-scale half-space generated by plotting the modulus of wavelet transform coefficient value, $|T(a,b)|$, for varying scales and locations. In the present invention, the scalogram may also be said to mean any suitably scaled power of $|T(a,b)|$.

A key advantage of wavelet-based techniques is the variety of wavelet functions available thus allowing the most appropriate to be chosen for the analysis of the signal under investigation. This is in contrast to Fourier analysis which is restricted to one feature morphology: the sinusoid. In some embodiments the Morlet wavelet is used. This is defined as:

$$\psi(t) = \pi^{-1/4}(e^{i2\pi f_0 t} - e^{-(2\pi f_0)^2/2})e^{-t^2/2} \qquad [2]$$

where $f_0$ is the characteristic, or central, frequency of the mother wavelet at scale a=1 and is chosen to best accentuate the features under investigation. In general, the characteristic frequency of a wavelet is inversely proportional to the wavelet scale.

Referring now to the drawings, FIG. 1 shows a schematic block diagram indicating the usage of a CPR analysis unit (5) within a defibrillator (2). The analogue electrocardiogram (ECG) and reference signals from a patient (1) are detected through sensors (3), via switching circuitry (8), to a monitoring circuit (9) where they are digitised. The embedded controller (4) passes selected segments of the ECG and reference signals to the CPR analysis unit (5) for analysis. In the preferred embodiment these segments will be of around 5 seconds in length with a sample rate of at least 100 Hz. The CPR analysis unit (5) passes back information concerning, at least one of: (i) the underlying rhythm, (ii) the efficacy of CPR and (iii) shock outcome prediction. The results of the analysis may then be presented to the device user through the User Interface (6) and/or used directly in the decision making process of a fully automated device. The decision to shock results in the defibrillation of the patient (1) though current discharged from the defibrillation circuitry (7) via the switching circuitry (8) to the electrodes (3).

Figure 2:
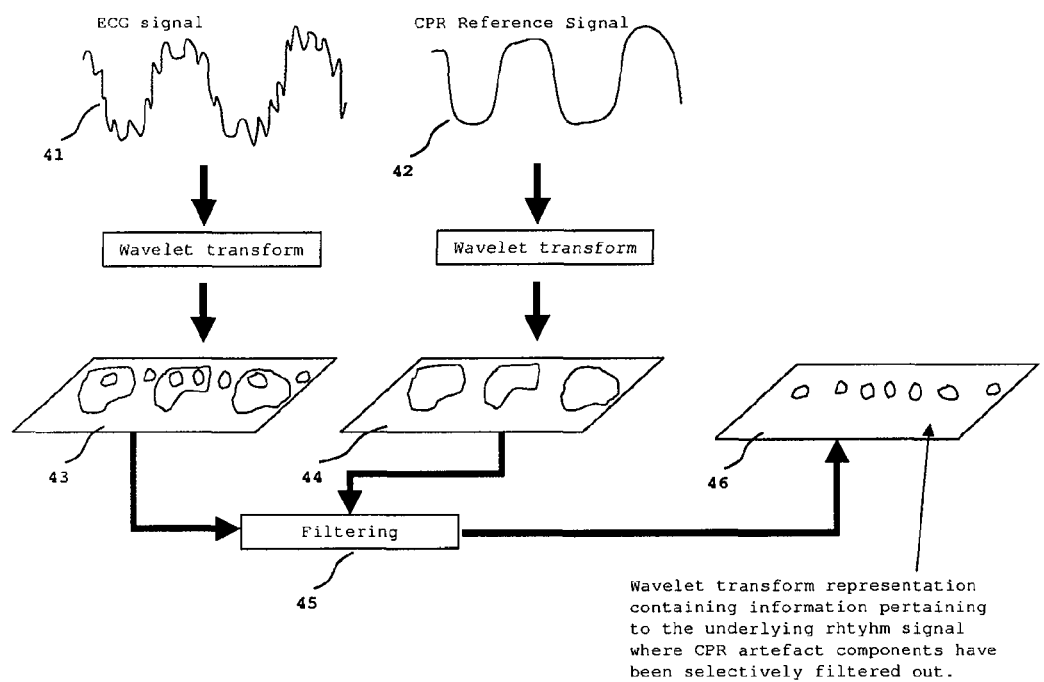
FIG. 2: Overview schematic of the wavelet transform filtering methodology.

An overview of the wavelet transform filtering methodology according to a particular embodiment is shown schematically in FIG. 2. The original ECG signal (41) and the CPR reference signal (42) are transformed into their respective wavelet representations (43) and (44). The wavelet transform derived from the CPR reference signal (44) is then used to filter (45) the wavelet representation of the ECG signal (43).

Here we define filtering as a process by which undesired signal artefact is suppressed (which can include complete negation of the components) from the signal of interest. The filtering process here will suppress the CPR artefact information from the original ECG signal. The filter then outputs information concerning the ECG signal where the CPR signal components have been suppressed (46). This filtered transform representation (46) is then analysed to provide information on the ECG signal components underlying the CPR artefact. The analysis produces 'characteristic measures' which can be used for one or more of the following (1) to identify the underlying rhythm, (2) to indicate the efficacy of CPR, and/or (3) to predict the outcome of a subsequent defibrillation shock.

The characteristic measures may include but are not limited to a temporal population statistic such as entropy, the standard deviation or other moment of distribution, or a value such as the maximum, minimum or mean value, the slope of a curve, etc.

The filtered transform representation (46) may take the form of a modified transform representation composed of modified components which may include values derived from the original or scaled transform components from the ECG and CPR signal, including but not limited to differences and ratios. More compact representations of the transforms used in the method illustrated in FIG. 2 may also be used including ridge and modulus maxima representations.

The modulus maxima, $T_m(a,b)$ are the loci of points describing the maxima of the scalogram surface. The modulus maxima are described by equation 3 below.

$$T_m(a, b) = |T(a, b)| \quad [3]$$

where $$\frac{d|T(a, b)|}{db} = 0$$

and $$\frac{d^2|T(a, b)|}{db^2} \neq 0$$

else $T_m(a, b) = 0$

Figure 3:
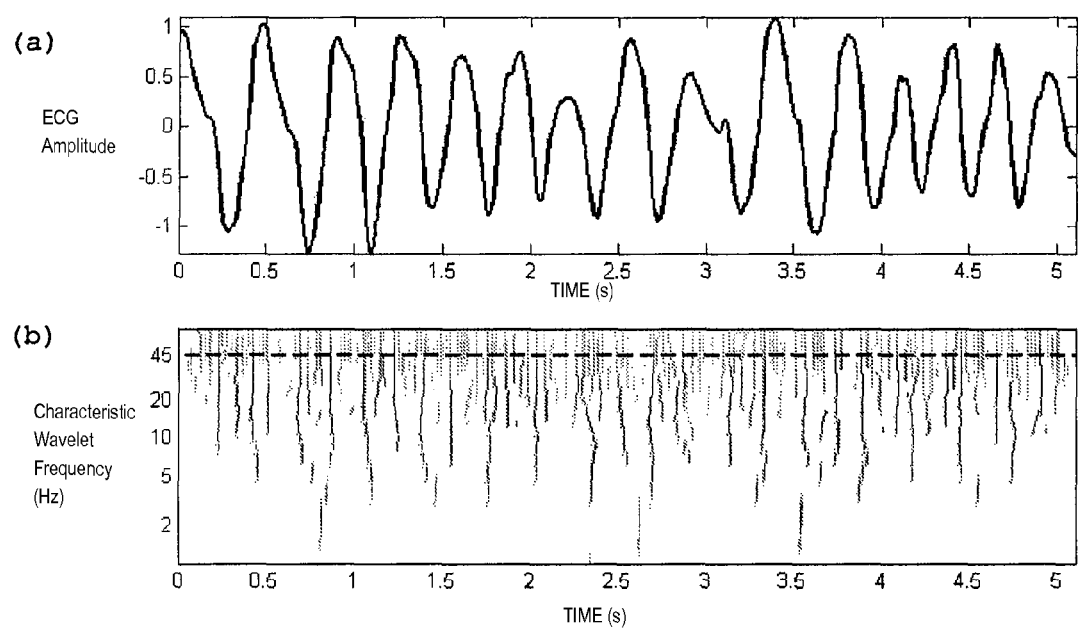
FIG. 3: (a) An ECG trace containing CPR artefact. (Horizontal axis=time in seconds. Vertical axis=ECG amplitude in arbitrary units.)

In one preferred embodiment the continuous wavelet transform of equation 1 is applied to the signal, employing the Morlet wavelet of equation 2. FIG. 3(a) shows an example of a section of digitised ECG containing CPR artefact with its associated wavelet scalogram modulus maxima plot shown beneath in FIG. 3(b). The lines running from top to bottom in the plot of FIG. 3(b) indicate the location of the modulus maxima. The signal segment shown in FIG. 3(a) was extracted from a human out-of-hospital data set containing 878 pre-shock ECG traces acquired from 110 patients with cardiac arrest of cardiac etiology. The data was recorded from the Medical Device Module of a Laerdal Heartstart 3000 defibrillator. A full review of the data acquisition procedure and statistics can be found in [5].

We can then filter out the effect of CPR artefact by identifying those modulus maxima lines which are associated with CPR and removing them from the analysis. One preferred method for achieving this is through the use of a reference signal that correlates well with CPR artefact. The reference signal can be for example but not limited to: accelerometer data, thoracic impedance data, and common mode voltages.

Figure 4:
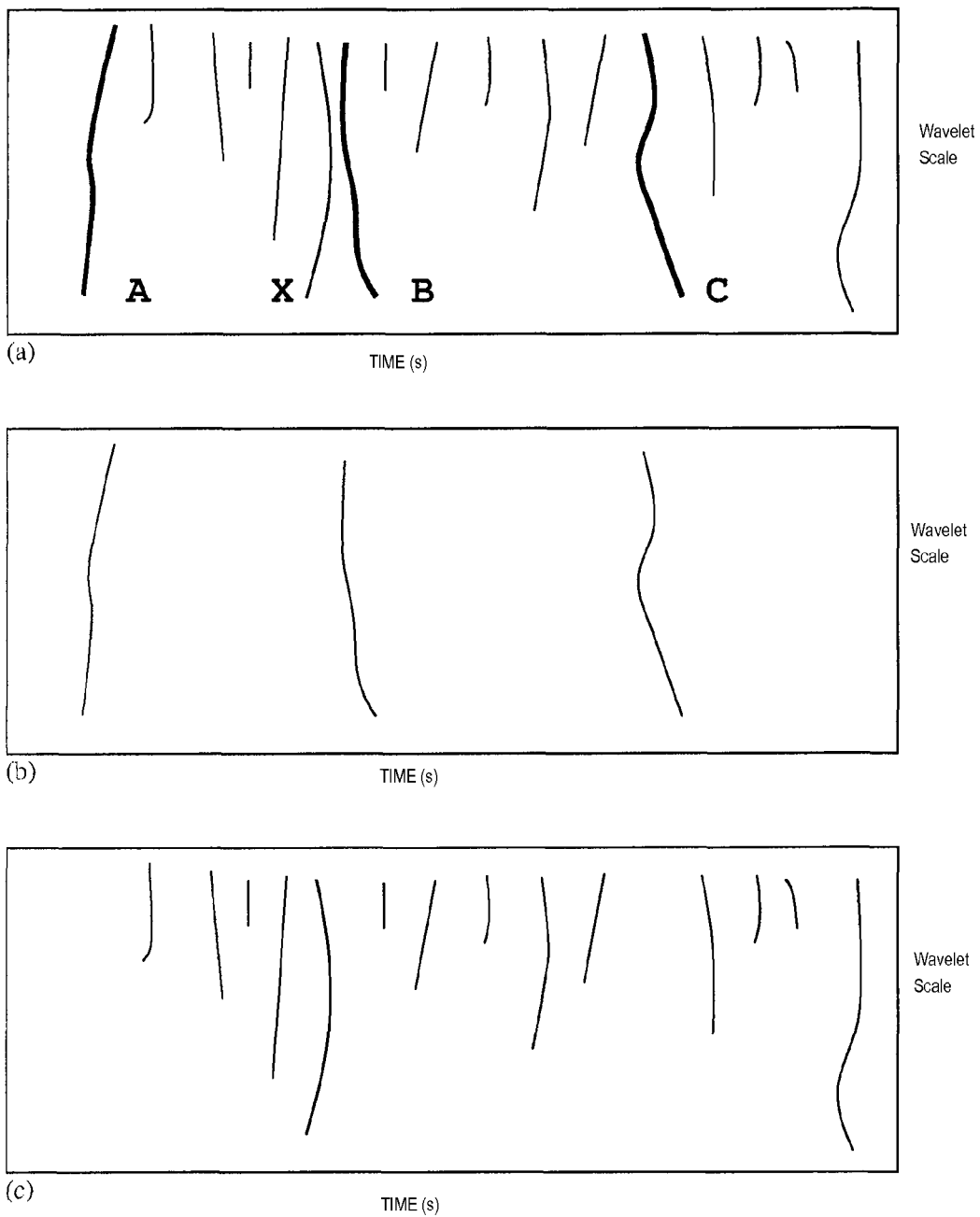
FIG. 4: (a) Schematic of the ECG modulus maxima surface (Horizontal axis=time in seconds. Vertical axis=wavelet scale.)

This method is shown schematically in FIG. 4. FIG. 4(a) contains the modulus maxima lines associated with an ECG signal containing CPR artefact. Modulus maxima lines marked A, B and C on the figure pertain to the CPR artefact.

The other lines (including the one marked X) correspond to other signal components which may include the underlying rhythm or high frequency signal noise. The modulus maxima line denoted X has similar characteristics to those of A, B and C but is not due to the CPR artefact and therefore contains information that is to be retained. FIG. 4(b) shows a schematic of the modulus maxima obtained from the CPR reference signal. These are coincidental with the lines A, B and C in the ECG modulus maxima plot of FIG. 4(a). The modulus maxima in FIG. 4(b) can therefore be used to identify correctly those lines associated with the CPR artefact. These can then be removed leaving the modulus maxima plot of FIG. 4(c). This contains lines which are not associated with the CPR artefact. These can then be analysed to provide a characteristic measure containing information pertinent to the classification of the underlying rhythm signal. The method is powerful in that the information contained in the modulus maxima line denoted X is left intact, whereas traditional methods including signal matching or frequency-filtering find it difficult to partition this information cleanly.

It will be recognised by those skilled in the art that in the above example the CPR reference signal may contain lines that are not exactly coincidental with lines A, B and C but from which the association with of lines A, B and C with CPR artefact can be inferred.

Analysis of the filtered wavelet transform coefficients to produce characteristic measures containing information relating to the underlying rhythm can include, but is not limited to: the interrogation of coefficient amplitude, frequency of occurrence, slope of the reordered coefficients, ratios of selected coefficients, and the entropy of the coefficients across scale or scales.

Other modulus maxima lines associated with large scale movement artefact may also be filtered out either through a correlation with those modulus maxima lines in the reference signal scalogram or by their own identifiable characteristics. In addition, shorter, low amplitude, modulus maxima ridges with components only in the low dilation (i.e. high characteristic frequency) region of the scalogram may be assumed to be electrical noise and removed. The remainder of the scalogram may then be analysed without the loss in performance associated with such noise.

The wavelet scale over which the analysis is performed depends upon the design characteristics of the defibrillator, such as analogue ECG signal conditioning (e.g. band-pass filtering, comb filtering); digital sampling rate; electrode size; electrode location; skin/electrode interface resistance. In the preferred embodiment a priori knowledge of these characteristics are used to identify optimal processing paths for calculating the characteristic measure. Typically we derive the pertinent information from the very small scale structures in the transform space. The scales from which the characteristic measure is derived will typically be of the order of that associated with a characteristic frequency of around 45 Hz.

Figure 5:
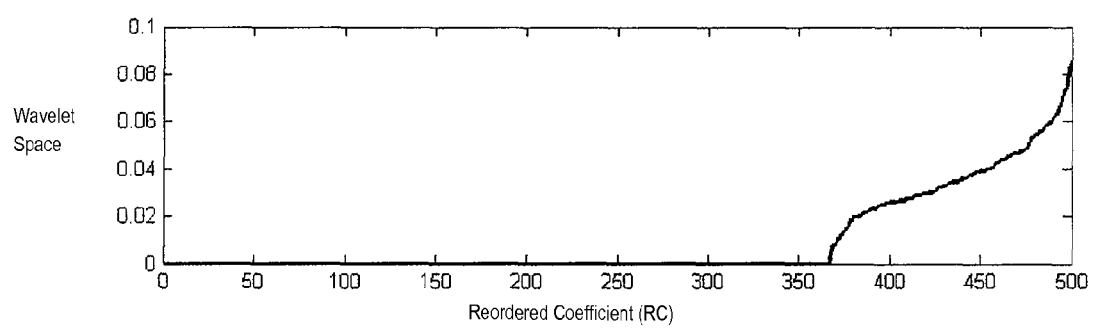
FIG. 5: Coefficient reordering curve obtained from the coefficients extracted at the level indicated by the horizontal dashed line in FIG. 3(b).

In an alternative embodiment, when no reference signal is available, all modulus maxima values at short temporal scales are selected. This is shown in FIG. 5 where the modulus maxima values at the level of the horizontal white band shown in FIG. 3(b) are selected. (In the preferred method these related to a characteristic wavelet frequency of the Morlet wavelet employed of 45 Hz.) The coefficients across this level are then extracted and reordered from smallest to highest as shown in FIG. 5. For the construction of this Reordered Coefficient (RC) curve, regions without a modulus maxima line across the selected level in FIG. 3(b) are set to zero value for the coefficient plot in FIG. 5. In this way we find that the coefficients relating to CPR and other signal components can be separated out for analysis.

Note that in the preferred method the temporal sampling of wavelet space is set to that of the sampling frequency of original signal of 100 Hz. Hence there are 500 reordered coefficients shown in FIG. 5 from the 5 second ECG trace analysed.

Figure 6:
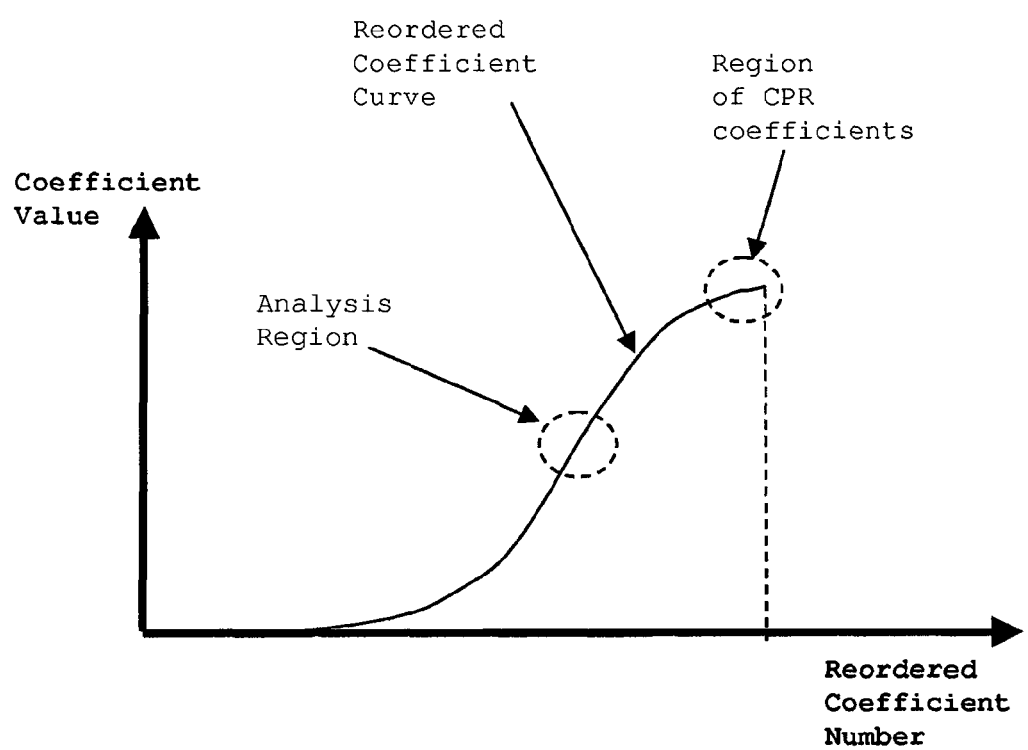
FIG. 6: Schematic of a coefficient reordering curve indicating Region of CPR Coefficients and the Analysis Region.

FIG. 6 shows a schematic of a curve obtained from coefficient reordering. From our studies of the curve we find that CPR is characterised by high energy modulus maxima lines which dominate the signal and are therefore to be found at the high end of the RC curve. The shape of the curve from the high value CPR coefficients is determined by the underlying rhythm. We have found from our studies of the ECG exhibiting various arrhythmias that VF gives a smoothly monotonic reduction in coefficient amplitudes whereas Asystole is characterised by a steep drops in coefficient values after the CPR coefficients. VT is characterised by a long plateau of coefficients after those associated with CPR whereas PEA is associated with a relatively short, and somewhat lower amplitude plateau of coefficients after those associated with CPR. Knowledge of the typical morphology of the RC curve for each rhythm type underlying CPR allows for their differentiation. This is achieved by selecting a region of the RC curve remote from the CPR region and characterising the curve at this point using a characteristic measure. This characteristic measure can be a measure of the amplitude of coefficients in this Analysis Region (shown in FIG. 6) and, or the slope of the curve in this region. The characteristic measure may also include measures of the relative properties of the analysis region coefficients to those within the CPR region. Other characteristic measures may be derived as appropriate without departing from the scope of the invention. In addition it will be recognised that characteristic measures from a plurality of analysis regions may be used in the method.

Rhythm Identification

Figure 7:
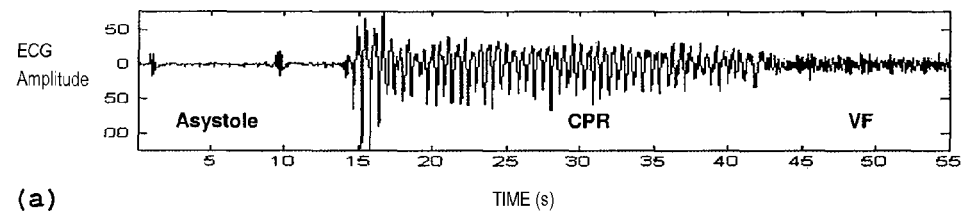
FIG. 7: (a) The ECG trace showing Asystole followed by a central region of CPR resulting in a VF waveform at the end of the trace. (Horizontal axis=time in seconds. Vertical axis=ECG amplitude in arbitrary units.)
Figure 7:
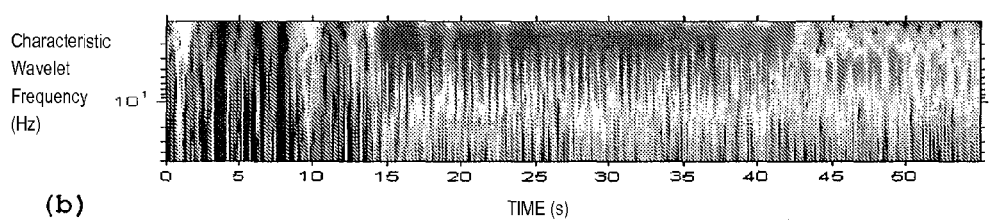
Figure 7:
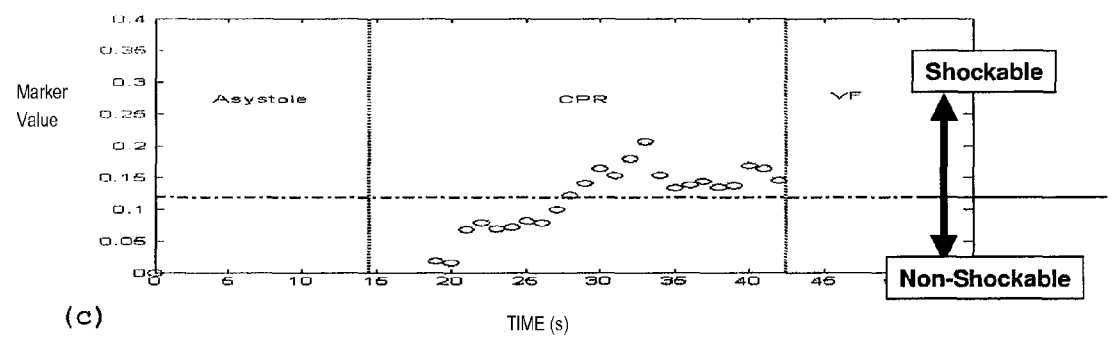

Once we have defined the characteristic measure to classify the underlying rhythm, it can be used to detect changes in underlying rhythm during CPR. This is shown in FIG. 7. FIG. 7(a) shows a segment of ECG signal containing a section of CPR with a pre-shock Asystole signal and a post-shock VF signal. That is, the ECG transitions from a non-shockable waveform to a shockable waveform during CPR. FIG. 7(b) shows the wavelet transform of the ECG signal over the same time period.

From the wavelet transform of the signal during CPR we derive our wavelet characteristic measure over signal windows of 5 seconds duration. The value of the characteristic measure is plotted against time in FIG. 7(c) with a single value being computed every second. We can see that there is a general increase in the characteristic measure value over time.

By defining a 'shockable-non-shockable threshold', as indicated by the horizontal dash-dot line in the plot, we can determine when the signal has transitioned to a shockable rhythm. In the practical application of the method CPR may be stopped at this point and a shock applied immediately. In another embodiment CPR may be stopped at this point and a second confirmatory rhythm identification undertaken in the absence of CPR.

The decision boundaries used for classifying ECG segments may be derived using standard regression or non-parametric statistical techniques—e.g. neural networks, Bayesian statistics. For the methods described here, segments of ECG with the same class of pre- and post-CPR rhythm were used to derive a linear threshold. The systems were then tested on segments of ECG where the pre- and post-CPR signals were of both the same and differing classifications such as that in FIG. 7(c) to ensure their applicability.

Efficacy of CPR

It can also be observed from FIG. 7(c) that there is a general increase in the characteristic measure value from 18 to 33 seconds. This change in the marker value over time can thus be used as an indication of the efficacy of CPR. An increase in characteristic measure value reflects a positive response to the applied CPR and, therefore, its efficacy.

Recent animal studies reported by Frenneaux [12] have shown trends in coronary perfusion pressure during CPR that closely follows trends identified by us in wavelet space [13]; c.f. FIG. 1 of Frenneaux and FIG. 3 of [13]. Indeed, we have also previously shown the correlation between topographical features in the ECG's wavelet scalogram and vessel pressure during VF [14] in similar animal studies. The Frenneaux paper also presents further evidence that the return of circulation post shocking is closely allied to this coronary perfusion pressure. Therefore, by following trends in the characteristic measures of this present invention it is possible to quantify the efficacy of the applied CPR.

It is proposed that the present invention can be used to more effectively close the CPR feedback loop. It is further proposed that the methods described provide a truer marker of CPR efficacy as they are derived from the patient's ECG (i.e. their measured response to therapy) rather than the currently employed proxy measures derived from the device's mechanical sensors (e.g. depth of compression).

Shock Outcome Prediction

Characteristic measures derived from the modulus maxima scalogram filtered to remove CPR artefact can also be used within a shock outcome prediction classification method, such as the one described in WO 2005/096170 by Addison and Watson. Further, alternative methods may also be employed to derive characteristic measures from the RC curve for use in the classification of shock outcome, including, for example, the amplitude and or the slope of the curve at a point outwith the CPR region. Alternatively, the original transform components may be analysed without undertaking a step of computing the modulus maxima representation.

Figure 8:
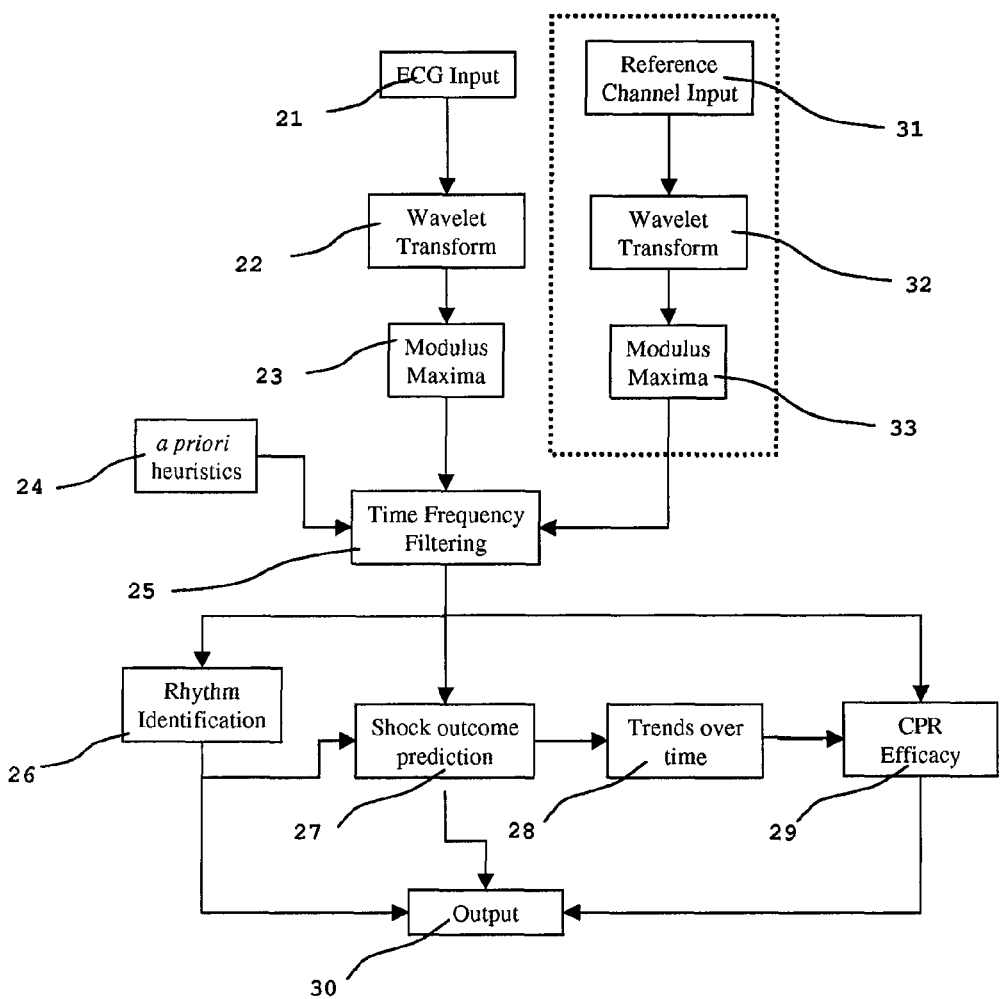
FIG. 8: Block diagram of the method for obtaining rhythm identification, shock outcome prediction and CPR efficacy.

FIG. 8 shows a flow diagram for the implementation of an embodiment of the method in practice. The ECG input (21) is transformed into a wavelet transform representation (22) from which the modulus maxima lines are computed (23). These are then sent to the time-frequency filtering module (25) for processing. Concurrently, the Reference Channel signal (31) which contains the signal that correlates well with CPR artefact is transformed into a wavelet transform representation (32) from which the modulus maxima lines are computed (33). These are also sent to the time-frequency filtering module (25) for processing. Within the time-frequency filtering module (25) the modulus maxima from the reference signal are then used to identify and remove those contained within the modulus maxima representation of the original ECG signal. The filtered modulus maxima are used to filter the ECG components according to predefined heuristics (24).

The time frequency filtered information can then be used to determine the underlying rhythm (26), predict the likely outcome of a subsequent defibrillation shock, and quantify the efficacy of the applied CPR. The trends over time of the characteristic measures may also be used to quantify CPR efficacy (29). The outputs: rhythm identification, shock outcome prediction and CPR efficacy can then be sent to an output module (30). This then forwards the information to the appropriate output mode, for example, to a visual display unit, to a control loop within a defibrillator unit for use in an automated system, etc.

In an alternative embodiment for use when there is no reference signal or where it is decided not to use the reference signal, the boxed components (31), (32) and (33) shown in the block diagram of FIG. 8 are not employed. The analysis is only performed using the ECG input signal. Accordingly a different set of heuristics (24) are used in the time-frequency filtering algorithm (25).

In another alternative embodiment, the use of modulus maxima representation may not be employed whereby the original transform representations of the ECG and CPR signals are used directly to compute a comparative measure between the ECG representation and the Reference Signal representation, or scaled version of these representations.

Summary

The preferred embodiment of the invention described herein are exemplar and numerous modifications, dimension variations, and rearrangements can be readily envisioned to achieve an equivalent result, all of which are intended to be embraced within the scope of this invention. In particular these modifications may relate to:
  the use of modulus maxima techniques for the reduction in computational efficiency.
  the type of resealing applied to the derived wavelet scalogram.
  the signal reconstruction post wavelet filtering for implementation with existing analysis methods.
  the use of alternative time-frequency transformations to achieve the localised signal partitioning of the CPR artefact from other signal components
  the use of alternative signal analysis tools to derive information from the high frequency (short time-scale) components of the signal to partition the CPR artefact from other signal components.

It will be recognised by those skilled in the art that the above analysis of the behaviour of the measures derived from the wavelet transform representation used identify (i) the underlying rhythm, (ii) determine the efficacy of CPR and, or, (iii) predict shock outcome can be performed using a multitude of signal processing methodologies including, but not limited to, those requiring iterative procedures.

It will be recognised by those skilled in the art that the method for partitioning the CPR signal from the underlying rhythm signal relies on the identification of short duration features (i.e. local features exhibiting high frequency spectral distributions) and characterisation of the signal by the same. Those skilled in the art will realise that, without departing from the spirit of the invention described herein, the use of the short duration signal features in this way can also be achieved using alternative transformations and other methodologies to isolate these features from the ECG signal.

It will be recognised by those skilled in the art that a plurality of reference signals may be used in the method without departing from the scope of the invention.

Various improvements and modifications can be made to the above without departing from the scope of the invention.

REFERENCES CITED

[1] Berg R A, Hilwig R W, Kern K B et al. Precountershock cardiopulmonary resuscitation improves ventricular fibrillation median frequency and myocardial readiness for successful defibrillation from prolonged ventricular fibrillation: a randomised, controlled swine study. Ann Emerg Med 2002; 40: 563-571.

[2] Achleitner U, Wenzel V, Strohmenger H U et al. The beneficial effect of basic life support on ventricular fibrillation mean frequency and coronary perfusion pressure. Resuscitation. 2001: 51:151-158.

[3] Kolarova J, Ayoub I M, Yi Z et al. Optimal timing for electrical defibrillation after prolonged untreated ventricular fibrillation. Crit Care Med. 2003; 31: 2022-2028.

[4] Eftestol T, Wik L, Sunde K, Steen P A. Effects of CPR on predictors of VF defibrillation success during out-of-hospital cardiac arrest. Circulation 2004; 110: 10-15.

[5] Sunde K, Eftestol T, Askenberg C, Steen P A. Quality assessment of defibrillation and advanced life support using data from the medical control module of the defibrillator. Resuscitation 1999; 41: 237-247.

[6] Wik L, Hansen T B, Fylling F, Steen T, Vaagenes P, Auestad B H, Steen P A. Delaying defibrillation to give basic cardiopulmonary resuscitation to patients with out-of-hospital ventricular fibrillation—A randomized trial. JAMA 2003; 289 (11): 1389-1395.

[7] Cobb L A, Fahrenbruch C E, Walsh T R et al. Influence of cardiopulmonary resuscitation prior to defibrillation in patients with out-of-hospital ventricular fibrillation. JAMA 1999; 1182-1188.

[8] Eftestol T, Sunde K, Steen P A. The effects of interrupting precordial compressions on the calculated probability of defibrillation success during out-of-hospital cardiac arrest. Circulation 2002; 105: 2270-2273.

[9] Aase S O, Eftestol T, Husoy J H, Sunde K, Steen P A, CPR artifact removal from human ECG using optimal multichannel filtering., IEEE Trans Biomed Eng. 2000 November; 47(11):1440-9.

[10] Eilevstjonn J, Eftestol T, Aase S O, Myklebust H, Husoy J H, Steen P A., Feasibility of shock advice analysis during CPR through removal of CPR artefacts from the human ECG. Resuscitation. 2004 May; 61(2):131-41

[11] Addison P S. The Illustrated Wavelet Transform Handbook: Introductory Theory and Applications in Science, Engineering, Medicine and Finance. Institute of Physics Publishing 2000; Bristol, UK.

[12] Frenneaux M, 'Cardiopulmonary resuscitation—some physiological considerations'; Resuscitation (58); 2003: 259-265

[13] Watson J N, Addison P S, Clegg G R, Holzer M, Sterz F and Robertson C E. A novel wavelet based analysis reveals hidden structure in ventricular fibrillation, Resuscitation 2000: 43:121-127.

[14] Addison P S, Watson J N, Clegg G R, Steen P A, Robertson C E. Finding Coordinated atrial activity during ventricular fibrillation using wavelet decomposition. IEEE Engineering in Medicine and Biology 2002; 21: 58-65.

The invention claimed is:

1. A method of signal analysis implemented using a computer processing device, said method comprising the steps of:
  deriving an electrocardiogram (ECG) signal from a subject during Cardio-Pulmonary Resuscitation (CPR);
  deriving a time-scale transform surface of the ECG;
  analyzing a characteristic measure of the time-scale transform surface of the ECG to identify an underlying myocardial rhythm, wherein the characteristic measure is derived from a set of coefficients of a modulus maxima representation which are re-ordered in order of magnitude;
  deriving a reference signal from the subject during CPR;
  deriving a time-scale transform surface of the reference signal; and using the time-scale transform surface of the reference signal to filter the time-scale transform surface of the ECG before analyzing said characteristic measure.

2. The method of claim 1, wherein the step of analyzing a characteristic measure of the time-scale transform surface comprises using empirically derived heuristics.

3. The method of claim 1, wherein said characteristic measure is obtained by a manipulation of coefficients obtained from the ECG time-scale surface calculated over one or more surface scales.

4. The method of claim 1, further comprising plotting said re-ordered coefficients as a curve, and wherein said characteristic measure is a slope across a selected portion of the curve.

5. The method of claim 1, further comprising plotting said re-ordered coefficients as a curve, and wherein said characteristic measure is a value of a single coefficient at a specified point in the curve.

6. The method of claim 1, further comprising plotting said re-ordered coefficients as a curve, and wherein said characteristic measure is a median, mode or mean of several values taken from a specified region on the curve.

7. The method of claim 1 whereby analysis is undertaken of the characteristic measure to determine whether the underlying myocardial rhythm is shockable or non-shockable.

8. The method of claim 7 wherein said analysis is characterized by a comparison of the characteristic measure against a threshold value.

9. The method of claim 1 wherein said underlying myocardial rhythm is one of ventricular fibrillation, ventricular tachycardia, asystole, pulseless electrical activity or a sinus rhythm.

10. The method of claim 9 wherein said analysis is characterized by a comparison of the derived characteristic measure against characteristics typical of the underlying myocardial rhythm.

11. The method of claim 10 where said characteristics typical of the underlying myocardial rhythm describe a shape of typical curves associated with the underlying myocardial rhythm types.

12. The method of claim 1, wherein said reference signal represents an electrical measurement.

13. The method of claim 12, wherein said electrical measurement is the subject's trans-thoracic impedance.

14. The method of claim 1, wherein said reference signal represents a mechanical measurement.

15. The method of claim 14, wherein said mechanical measurement is a force measurement of a chest during CPR.

16. The method of claim 15, wherein said force measurement is obtained from strain gauge sensors.

17. The method of claim 14, wherein said mechanical measurement is derived from an acceleration measurement of the subject during CPR.

18. The method of claim 1, wherein the step of filtering the time-scale transform surface of the ECG comprises cancelling or negating of coefficient values within the time-scale transform surface of the ECG when coefficient values in the reference signal's transform surface that are proximal in time and scale to the coefficient values within the time-scale transform surface of the ECG fulfill a predetermined criterion.

19. The method of claim 18, wherein said criterion is a coefficient amplitude being above a given threshold.

20. The method of claim 1, wherein the step of filtering the time-scale transform surface of the ECG comprises scaling of coefficient values within the time-scale transform surface of the ECG with respect to the coefficient values in the reference signal's transform surface which are proximal in time and scale.

21. The method of claim 1, wherein the step of filtering the time-scale transform surface of the ECG comprises a suppression of redundant coefficient values within the time-scale transform surface of the ECG.

22. The method of claim 21, wherein said suppression of coefficient values utilizes modulus maxima techniques.

23. The method of claim 1, wherein said time-scale transform is a wavelet transform.

24. The method of claim 23, wherein said wavelet transform is a continuous wavelet transform.

25. The method of claim 1 wherein said characteristic measure includes a median coefficient value of a number of one or more highest coefficient values from one or more ECG time-scale scales.

26. The method of claim 25, wherein said characteristic measure is computed from coefficients associated with scales with characteristic frequencies above that of a typical fibrillating frequency of a heart.

27. The method of claim 25, wherein said characteristic measure is computed from coefficients associated with scales of characteristic frequencies above that of a typical frequency of CPR.

28. The method of claim 1, wherein the said characteristic measure includes an entropy measure.

29. The method of claim 28, wherein said entropy measure is of the form:

$$WE_a = \frac{\int \ln|T(a, b)|_a \, db}{\int |T(a, b)|_a \, db}$$

wherein $WE_a$ is the entropy measure and $|T(a,b)|_\alpha$ is a wavelet transform modulus value.

30. The method of claim 28, wherein said entropy measure is computed from coefficients associated with scales with characteristic frequencies above that of a typical fibrillating frequency of a heart.

31. A method of signal analysis according to claim 1, further comprising the step of analyzing the measured characteristic to determine an ongoing efficacy of CPR.

32. A method of signal analysis according to claim 1, further comprising the step of analyzing the measured characteristic to perform a defibrillation shock outcome prediction.

33. An apparatus for signal analysis comprising:
a sensor configured to derive an electrocardiogram (ECG) signal from a subject during Cardio-Pulmonary Resuscitation (CPR); and
a computer processing device configured to:
derive a time-scale transform surface of the ECG;
analyze a characteristic measure of the time-scale transform surface of the ECG to identify an underlying myocardial rhythm, wherein the characteristic measure is derived from a set of coefficients of a modulus maxima representation which are re-ordered in order of magnitude;
derive a reference signal from the subject during CPR;
derive a time-scale transform surface of the reference signal; and
use the time-scale transform surface of the reference signal to filter the time-scale transform surface of the ECG before analyzing said characteristic measure.

34. A defibrillator comprising the apparatus of claim 33.

35. The apparatus of claim 33, wherein analyzing a characteristic measure of the transform surface comprises using empirically derived heuristics.

36. The apparatus of claim 33, wherein said characteristic measure is obtained by a manipulation of coefficients obtained from the ECG time-scale surface calculated over one or more surface scales.

37. A computer program product comprising at least one non-transitory computer-readable medium encoded with instructions to cause a computer processing device to perform a method comprising:
- deriving an electrocardiogram (ECG) signal from a subject during Cardio-Pulmonary Resuscitation (CPR);
- deriving a time-scale transform surface of the ECG;
- analyzing a characteristic measure of the time-scale transform surface of the ECG to identify an underlying myocardial rhythm, wherein the characteristic measure is derived from a set of coefficients of a modulus maxima representation which are re-ordered in order of magnitude;
- deriving a reference signal from the subject during CPR;
- deriving a time-scale transform surface of the reference signal; and
- using the time-scale transform surface of the reference signal to filter the time-scale transform surface of the ECG before analyzing said characteristic measure.

38. The computer program product of claim 37, wherein analyzing a characteristic measure of the transform surface comprises using empirically derived heuristics.

39. The computer program product of claim 37, wherein said characteristic measure is obtained by a manipulation of coefficients obtained from the ECG time-scale surface calculated over one or more surface scales.

* * * * *